United States Patent [19]

McAleer et al.

[11] Patent Number: 5,876,577
[45] Date of Patent: Mar. 2, 1999

[54] ELECTROCHEMICAL OXYGEN SENSOR

[75] Inventors: Jerry McAleer; Martin Ackland, both of Oxon, England

[73] Assignee: Cranfield Biotechnology Ltd., England

[21] Appl. No.: 809,627

[22] PCT Filed: Sep. 28, 1995

[86] PCT No.: PCT/GB95/02299

§ 371 Date: Sep. 23, 1997

§ 102(e) Date: Sep. 23, 1997

[87] PCT Pub. No.: WO96/10174

PCT Pub. Date: Apr. 4, 1996

[30] Foreign Application Priority Data

Sep. 28, 1994 [GB] United Kingdom ............... 9419513

[51] Int. Cl.$^6$ .................................................. G01N 27/26
[52] U.S. Cl. ............... 204/418; 204/412; 204/424; 204/403; 204/431; 205/782; 205/784; 205/785.5; 205/789; 205/792; 205/792.5
[58] Field of Search .................................... 204/403, 412, 204/415, 416, 418, 431, 424; 205/782, 782.5, 783, 783.5, 784, 785.5, 792, 792.5, 789; 422/79, 82.04

[56] References Cited

U.S. PATENT DOCUMENTS

| 4,225,401 | 9/1980 | Pace ......................................... 204/412 |
| 4,407,907 | 10/1983 | Takamura et al. ......................... 429/42 |
| 4,957,615 | 9/1990 | Ushizawa et al. ...................... 204/415 |
| 5,120,421 | 6/1992 | Glass et al. ............................. 204/412 |

Primary Examiner—Bruce F. Bell
Attorney, Agent, or Firm—Beyer & Weaver, LLP

[57] ABSTRACT

An electrochemical oxygen sensor comprises an impermeable substrate and a plurality of conductive layers applied thereto by thick film deposition. At least one conductive layer comprises an electrode and a conductor connected to the electrode. The electrode may have a covering layer of an ion exchange polymer.

9 Claims, 4 Drawing Sheets

ELECTROCHEMICAL OXYGEN SENSOR

This application is a 371 of PCT/GB95/02299 filed Sep. 28, 1995.

This invention relates to an electrochemical oxygen sensor adapted to detect gaseous or dissolved oxygen. The sensor may also detect other reducible chemical species. The invention also relates to manufacture of such sensors by thick layer deposition including printing techniques.

Conventional oxygen sensors are constructed from a multiplicity of components in the form of a reusable Clark cell. Clark sensors are expensive to construct and require frequent maintenance by skilled technicians. In particular the electrolyte gel and gas permeable membrane may need regular attention.

According to a first aspect of the present invention an electrochemical oxygen sensor comprises an impermeable substrate and a plurality of conductive layers applied thereto by thick film deposition, at least one conductive layer comprising an electrode and a conductor connected to the electrode.

A sensor in accordance with this invention can be manufactured economically by screen printing or other lithographic techniques. Electrosensors may be disposable before maintenance becomes necessary. Miniaturisation of a sensor is facilitated. The sensors can be fabricated as microelectrode arrays as disclosed in WO91/08474. The active area of the sensor may be manufactured by printing or ink jet methods and appropriate layers may be applied as described below so that the sensor can detect oxygen and reducible species in aqueous or other condensed phases. Coupling the oxygen sensor to other reagents that either consume or release oxygen, for example enzymes, allows detection of a wide range of analytes.

Sensors in accordance with the present invention have the advantage that it is not essential to provide a membrane as must be used in conventional Clark cells. This simplifies manufacture and enhances the sensitivity of the sensors.

Furthermore the sensors have the surprising ability to detect and measure dissolved oxygen in biological fluids for example foodstuffs such as milk, food slurries or other food products and physiological specimens.

The impermeable substrate preferably provides a planar surface upon which the conductive components may be deposited. A laminar substrate is preferred. Plastic substrates may be employed together with coatings of materials which do not require curing at high temperatures. Alternatively ceramic substrates can be used with high temperature resistant coatings.

According to a preferred aspect of the present invention an electrochemical oxygen sensor comprises an impermeable substrate and a plurality of conductive films disposed on the substrate and arranged to form a multiplicity of electrochemical electrodes in use.

The sensor preferably includes contacts for attachment to a detector circuit.

The electrodes can be applied to the substrate to form an array of individual sensors. The device can then be mechanically formed, for example by thermoforming or by bonding of a further layer which may overlie the conductive layers to define an array of wells or receptacles. Such an array can be used for a variety of simultaneous or successive analyses. For example microbial enumerations, chemical and toxin determinations, antibiotic arrays and substrate determinations may be facilitated.

According to a second aspect of the present invention a method of manufacture of an electrochemical oxygen sensor comprises the steps of providing an impermeable substrate, forming a plurality of conductive layers by thick film deposition on the substrate, at least one conductive layer comprising a redox electrode and a conductor connected to the electrode A variety of techniques may be used to form the electrodes, including printing, for example screen printing, lithography, ink jet and flexographic printing. Various coating methods for example dipping, spraying, spin coating and dosing may also be employed. Distortion printing can be employed if physical deforming is used to construct the wells or receptacles. Conventional flexible printed circuit board techniques can be used in the construction of sensors in accordance with this invention.

According to a preferred aspect of the present invention an electrochemical oxygen sensor comprises an impermeable substrate layer, a plurality of electrode layers and a layer of active material overlaying one of said electrode layers wherein the electrodes and active layers comprise films deposited on an underlying surface. The underlying surface may comprise the substrate or a film deposited over the substrate.

The active material may comprise a polymer which is selectively permeable to cations and polar species but impermeable to anionic and non-polar compounds. Preferred active layers comprise ion exchange polymers especially perfluoritnated ion exchange polymers for example Nafion or Promeon (Trade Marks). Use of a cationic polymer affords a sensor adapted to detect oxygen in liquid or other condensed analytes by prevention of the latter from contacting the electrode surface. Nafion is a copolymer of tetrafluoroethylene and perfluoro[2-(fluorosulphonyl ethoxy)propyl vinyl] ether manufactured by Dupont. Alternative sulphonated fluorocarbon polymers may be employed. oxygen may be determined by direct electrochemical reduction or by means of its effect on oxygen reduction catalyst. Such an intermediate species is sensitive to oxygen. Especially preferred oxygen reduction catalysts include cobalt (II) porphyrin compounds for example cobalt (II) tetraaminophenyl porphyrin. Amine complexes of cobalt eg hexaamino cobalt (II) may also be employed.

Sensors in accordance with this invention have the advantage of ease of sterilisation. Individual electrodes or electrode arrays can be sealed into a bag, other container or packaging to facilitate thermal, chemical or radiation sterilisation. Such procedures cannot be used with a conventional Clark electrode.

In a preferred embodiment of this invention sensor apparatus includes an oxygen sensor as previously described together with a detector circuit, the circuit being adapted to apply a potential to the electrode relative to a reference or counterelectrode and further adapted to measure the current after a period of equilibration.

In particularly preferred embodiments the control circuit is adapted to apply two or more potentials to the electrodes and to measure the respective currents at these potentials. Measurement at two potentials can avoid false results due to reduction of contaminant species. For example measurements may be carried out at −800 mV at which contaminants caused by microbial metabolism are also reduced in addition to oxygen. oxygen is not reduced at −500 mV. The making of two measurements at −500 mV and −800 mV allows the contribution due to the metabolites to be determined and the oxygen level measured. More than two potentials may be employed to differentiate various reducible contaminants from oxygen.

A particular application of this invention is in the detection of spoilage, for example of an aseptically packaged product such as UHT milk or other food product. A simple electrode for example having no additional layers, can detect oxygen or other reducible species in the product contained in such packaging. The absence of additional layers allows rapid equilibration so that a test can be carried out within a few seconds. In such an assay the absence of reducible species can indicate that the growth of micro-organisms has taken place. Conventional methods for testing such products include pH measurement which has been shown to be a very poor indicator of spoilage and ATP measurement via bioluminescence which is expensive and suffers from interference by somatic ATP. In contrast oxygen determination using disposable electrodes in accordance with this invention is inexpensive, rapid and reliable. These factors allow for more statistically significant sampling procedures to be adopted than has been previously possible.

A further use of sensors in accordance with this invention is for determination of the oxygen content of gaseous media. There are many known solid state oxygen sensors, for example using yttria stabilised zirconia but these are ceramic devices which operate at high temperatures. Deposition of a polymer electrolyte onto an electrode in accordance with the present invention facilitates production of a disposable solid state amperometric oxygen sensor which may be operated at room temperature.

Formation of sensors in accordance with this invention into a tray defining a multiplicity of receptacles each including a sensor affords a convenient laboratory device for microbial enumeration, biological oxygen demand (BOD) and toxicity testing and determination of antibiotic activity. There are many further applications for such an array. The receptacles of an array may contain media having different concentrations of an antibiotic substance inoculated with a micro-organism. Growth of the micro-organism can be detected by a reduction in the electrochemically determined oxygen level of the medium. A rapid and simple method of assessment of the sensitivity of an organism to an antibiotic is afforded. Sensors in accordance with this invention may be used for determination of residual antibiotics, for example in food products such as milk.

BRIEF DESCRIPTION OF THE DRAWINGS

The invention is further described by means of example but not in any limitative sense, with reference to the accompanying drawings of which.

Figure 1:
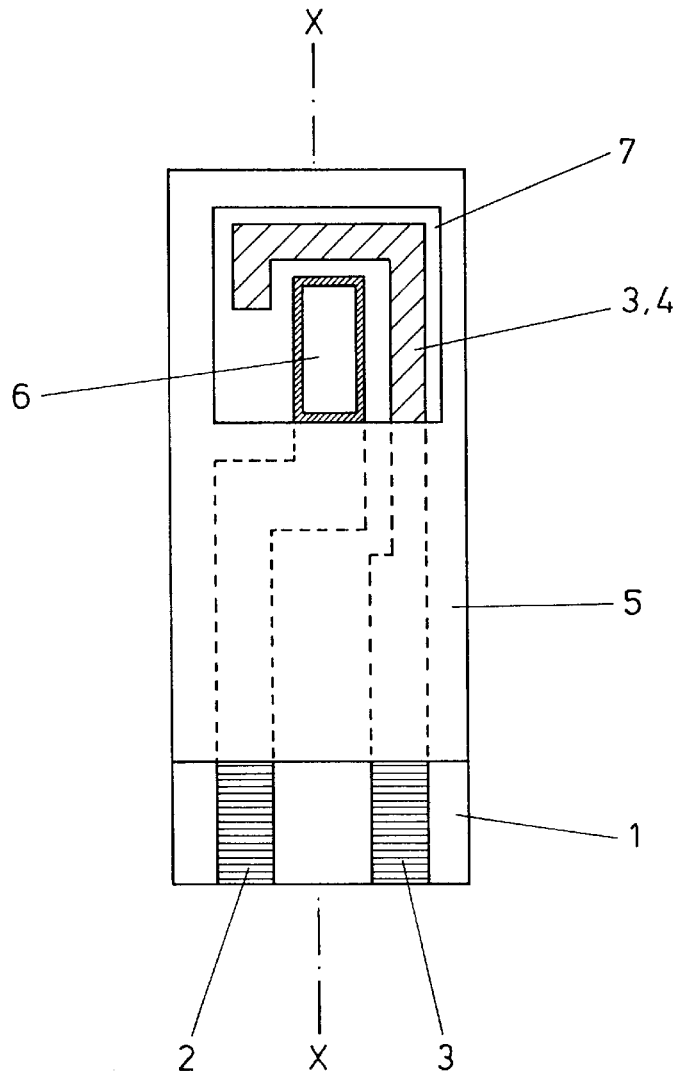
FIG. 1 is a plan view of a sensor in accordance with the present invention.
Figure 2:
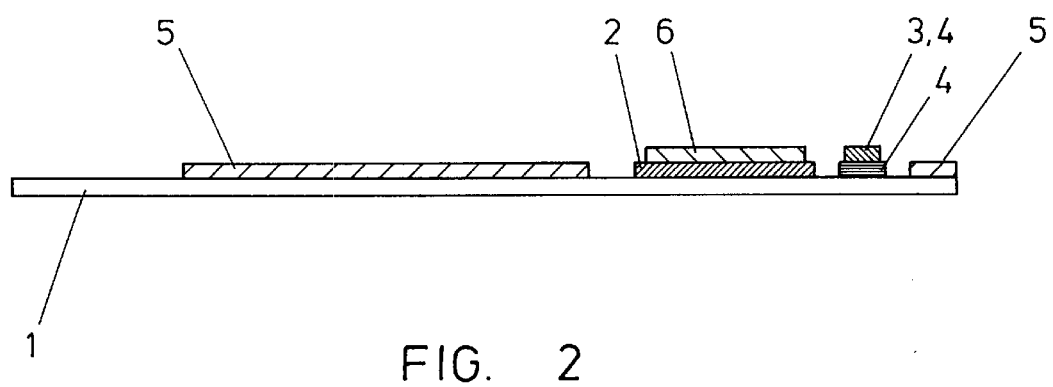
FIG. 2 is a cross-section on X—X of the sensor shown in FIG. 1.

The sensor shown in FIGS. 1 or 2 has an active layer 6 in the sensing region 7 directly exposed to the analyte. The planar substrate 1 is composed of a polymeric material, for example polyester or polycarbonate a cellulose material for example paper or card or a ceramic. Conductive films 2 and 3 are formed of any suitable conducting ink, for example carbon, silver, platinum or gold inks are disposed on the substrate. The sensing region 7 comprises an active layer 6, counter electrode 3 and reference electrode 4. The counter electrode 3 and reference electrode 4 may be combined as shown or may be provided as separate electrodes. The reference electrode 4 may be formed from an ink containing silver and silver chloride. Alternatively the silver chloride may be electrolytically deposited. The active layer 6 may comprise a surface on which oxygen can be reduced. Silver, gold, platinum, iridium or lead surfaces may be employed. Carbon may also be employed. An insulating layer S serves to shield the conductors from the analyte.

Figure 3:
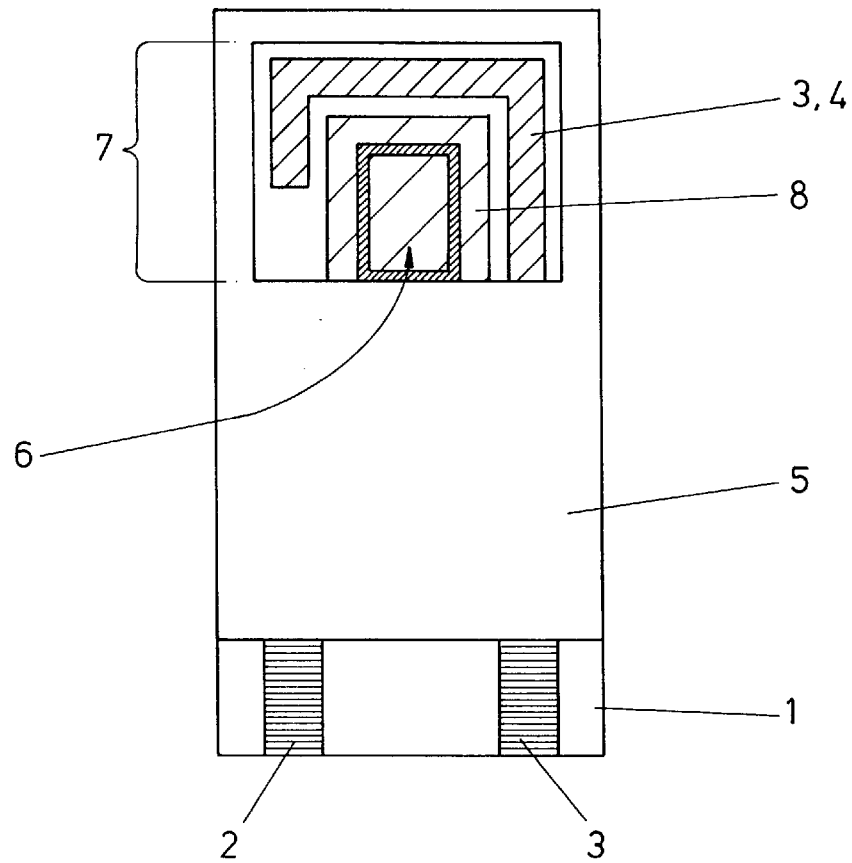
FIG. 3 is a plan view of a printed sensor with additional layers.
Figure 4A:
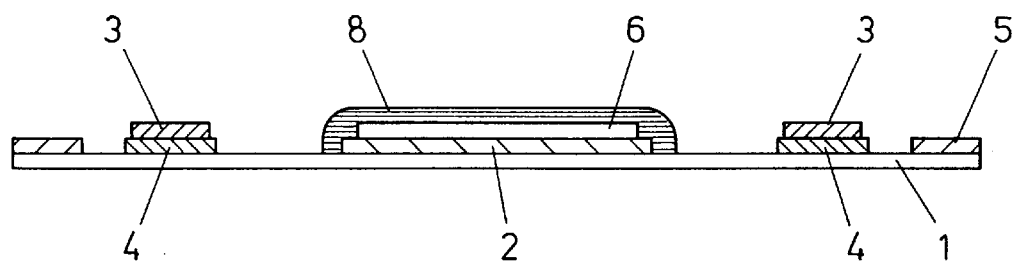
FIGS. 4a and 4b show cross-sectional views of sensors having additional layers.
Figure 4B:
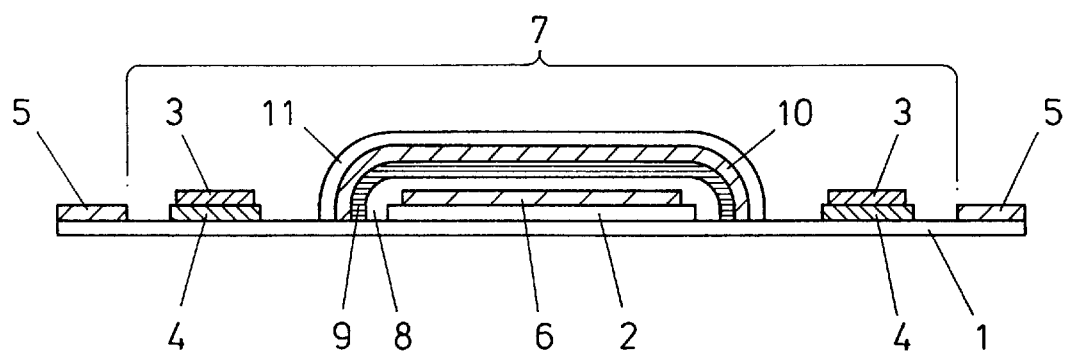

FIGS. 3, 4a and 4b show a more complex construction wherein the active layer 6 is coated with a selective layer 8. The selective layer may be a multi-layer structure as shown in FIG. 4b wherein four selective layers 8, 9, 10 and 11 are shown. Any number of selective layers may be employed. The selective layers 8 to 11 can be deposited by screen printing, ink jets, spray, airbrush dipping or dosing techniques. Alternative techniques can be employed. The selective layers may have a variety of compositions.

Cationic polymer electrolytes, for example Nafion and Promeon (Trade Marks) may be employed to detect oxygen in the gaseous phase. A permeable cellulosic layer, for example cellulose acetate, ethyl hydroxy ethyl cellulose, etc may be used to ensure that ionic reducible and high molecular weight substances do not contact the underlying active layer.

Enzymes, for example glucose oxidase which consume oxygen when reacting with their specific substrate may be incorporated into a selective layer. The substrate may be measured by this means by detection of depletion of oxygen.

Organelles for example chloroplasts and mitochondria may be incorporated into a selective layer. Photosynthetic organisms may be used, the interruption of photosynthesis serving to indicate toxicity of the analyte. Micro-organisms may be incorporated into the selective layer and changes in microbial respiration can be used to indicate the presence of toxins, antibiotics and metabolisable substrates.

Manganese dioxide or other agents may be incorporated into a selective layer to allow determination of hydrogen peroxide or hydroperoxides.

Figure 5:
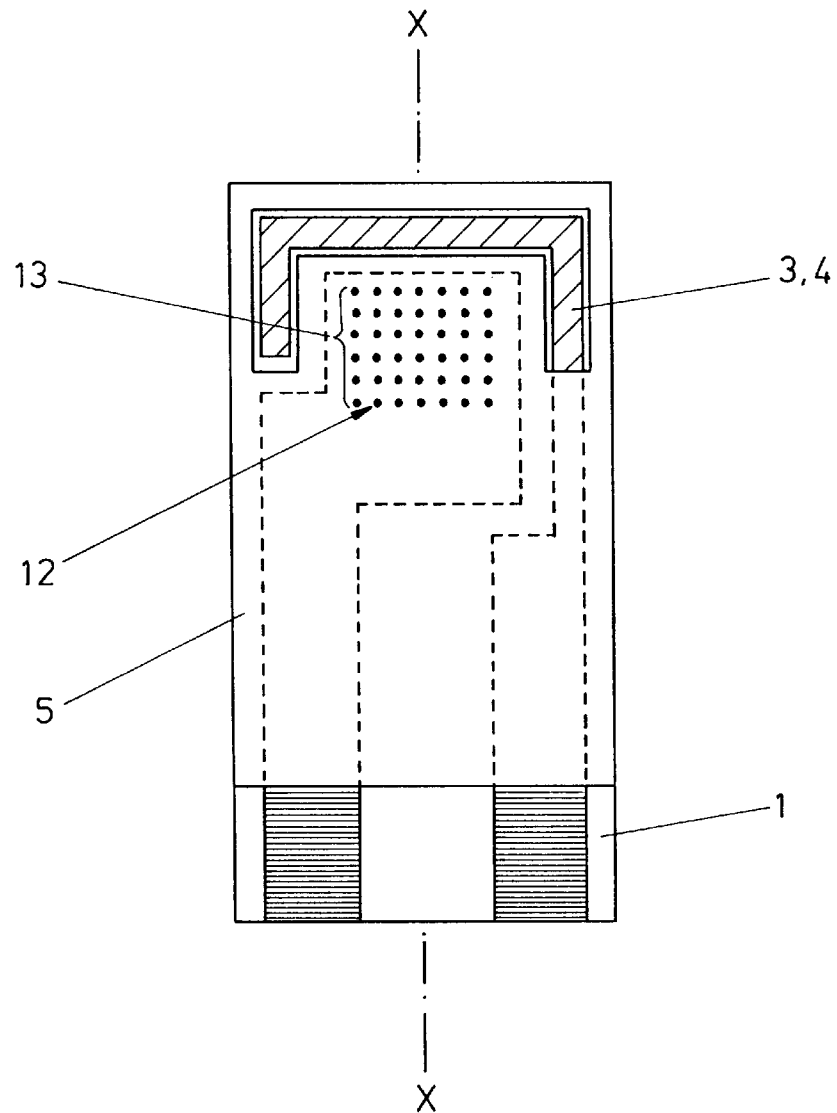
FIG. 5 illustrates a sensor having micro-electrodes in the sensing region.
Figure 6:
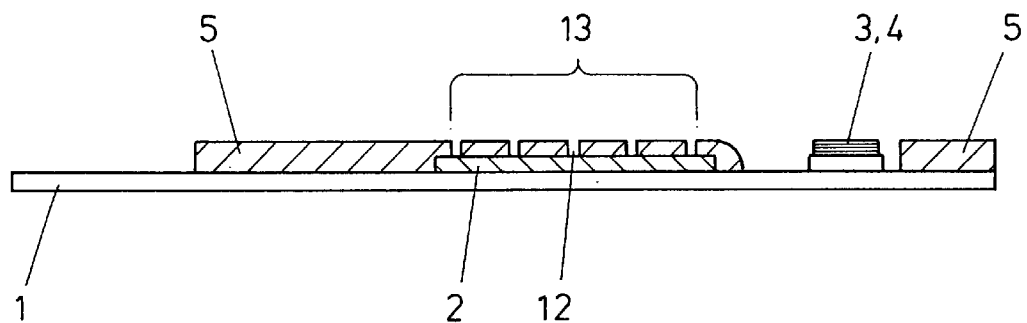
FIG. 6 is a cross-section of a sensor shown in FIG. 5.

FIGS. 5 and 6 show the use of microelectrodes 12 in an array 13. The microelectrodes can vary in size and diameter for example having a dimension of 20 μm. Such microelectrodes may be formed by laser ablation as disclosed in WO91/08474, the disclosure of which is incorporated into this specification by reference. Use of microelectrodes affords the benefit that the amount of reducible material consumed during the measurement is minimised enabling continuous measurement without perturbation of equilibria in the analyte. The number and dimensions of the electrodes may be selected in accordance with the performance characteristics required. Microelectrodes 12 may extend through the insulating layer 5 to the active layer to form an array 13. A microelectrode array may be coated with overlayers of selected materials (not shown) as previously described. The conductive layers 2 may be formed from printed carbon ink in a conventional manner. Manufacture by a laser ablation is facilitated by selection of an appropriate material for the insulating layer 5, for example, parylene.

Figure 7:
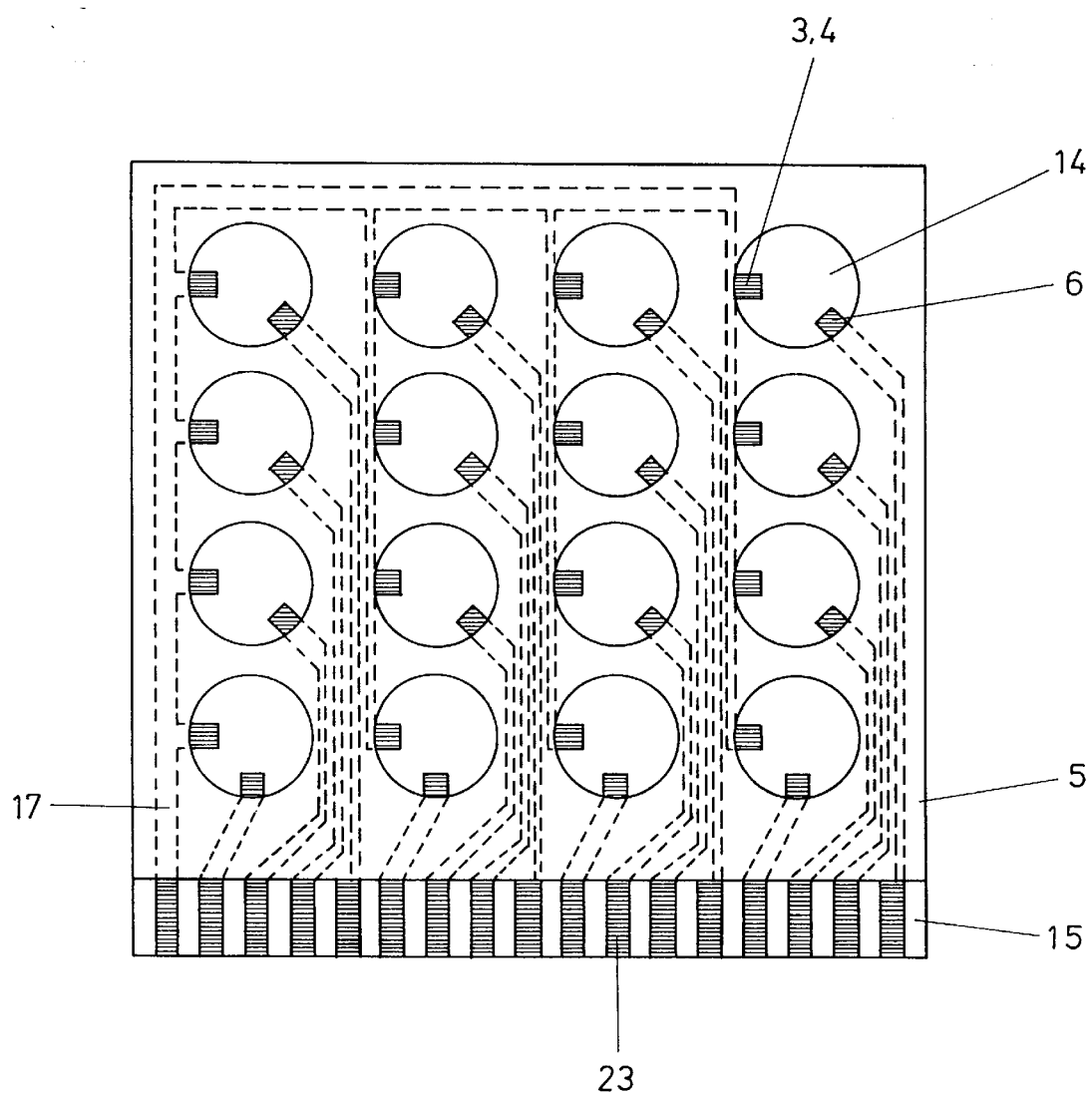
FIG. 7 shows an array of printed electrodes formed to make a series of wells.
Figure 8:
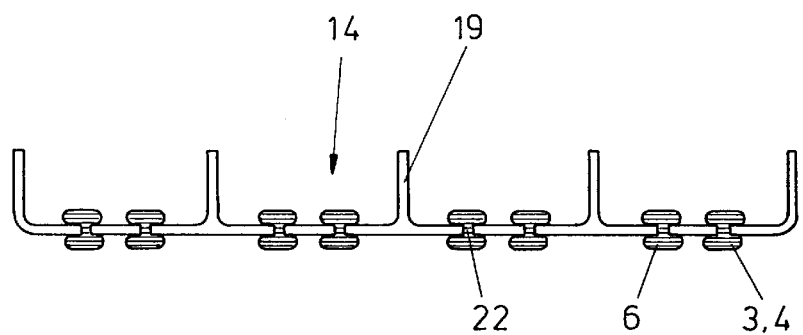
FIG. 8 is a cross-section of a sensor shown in FIG. 7.

FIGS. 7 and 8 illustrate an array of cells wherein each cell 14 has an electrode including an active layer 6 and a combined counter and reference electrode 3, 4. The electrodes 3, 4 are connected to an edge connector 15 by means of conductors 16 and 17. In a preferred embodiment the conductors 16 and 17 are printed on the upper surface of a laminar substrate which is subsequently deformed to provide the array of wells. Alternatively an additional layer comprising the well walls 19 may be secured to the substrate as a subsequent step. In this embodiment the conductors 16 and 17 are insulated from the environment by printing a dielectric layer so that the conductors are exposed only at the cell and connector ends. Alternatively the conductors 16 and 17 can be printed onto the underlayer of the substrate and the electrical connection can be made by means of holes 22. In a simple arrangement, the electrodes can have an integral common construction 17 to allow use of less complex contacts 23 and ancillary detector circuitry (not shown).

We claim:

1. An electrochemical oxygen sensor comprising an impermeable substrate and a plurality of conductive layers, at least one conductive layer comprising an electrode and a conductor connected to the electrode, the sensor further comprising a layer of active material overlaying said electrode, wherein the active material comprises an ion exchange polymer and wherein the active layer includes an oxygen reduction catalyst.

2. A sensor as claimed in claim 1, wherein a multiplicity of conductive films are disposed on the substrate and arranged to form a plurality of electrochemical electrodes.

3. A sensor as claimed in claim 2, including a further layer defining an array of receptacles.

4. A sensor as claimed in claim 1, wherein the oxygen reduction catalyst is cobalt (II) tetraaminophenyl porphyrin.

5. A sensor as claimed in claim 1 wherein the conductor is carbon or silver.

6. A sensor as claimed in claim 1, wherein the sensor does not include a gas permeable membrane overlying the electrode.

7. A sensor as claimed in claim 1, including a detector circuit adapted to be connected in use to said conductor, the detector circuit being arranged to detect electrochemical reduction at said electrode at two or more voltages.

8. A method of detecting an amount of dissolved oxygen in a biological fluid, comprising providing an electrochemical oxygen sensor including an impermeable substrate and a plurality of conductive layers applied thereto by thick film deposition, at least one of said conductive layers including an electrode and a conductor connected to the electrode, the sensor further including a layer of active material overlaying said electrode, wherein the active material comprises an ion exchange polymer and wherein the active layer includes an oxygen reduction catalyst; and exposing the biological fluid to the active layer.

9. The method of claim 8, wherein the biological fluid is a foodstuff.

* * * * *